United States Patent
Dubois et al.

(10) Patent No.: US 9,914,699 B2
(45) Date of Patent: Mar. 13, 2018

(54) PROCESS OF DEHYDRATION REACTIONS

(75) Inventors: Jean-Luc Dubois, Millery (FR);
Kimito Okumura, Yamaguchi (JP);
Yasushi Kobayashi, Yamaguchi (JP);
Ryota Hiraoka, Yamaguchi (JP)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/234,661

(22) PCT Filed: Jul. 27, 2012

(86) PCT No.: PCT/IB2012/001574
§ 371 (c)(1),
(2), (4) Date: Apr. 11, 2014

(87) PCT Pub. No.: WO2013/017942
PCT Pub. Date: Feb. 7, 2013

(65) Prior Publication Data
US 2014/0213811 A1 Jul. 31, 2014

(30) Foreign Application Priority Data
Jul. 29, 2011 (WO) .................. PCT/IB2011/002068

(51) Int. Cl.
| | | |
|---|---|---|
| C07C 253/26 | (2006.01) |
| C07C 51/16 | (2006.01) |
| C07C 253/24 | (2006.01) |
| C07C 51/347 | (2006.01) |
| C07C 45/52 | (2006.01) |
| C07C 51/25 | (2006.01) |

(52) U.S. Cl.
CPC ............ *C07C 253/26* (2013.01); *C07C 45/52* (2013.01); *C07C 51/16* (2013.01); *C07C 51/252* (2013.01); *C07C 51/347* (2013.01)

(58) Field of Classification Search
CPC ... C07C 255/00; C07C 253/00; C07C 253/26; C07C 253/24; C07C 51/16; C07C 51/252; C07C 51/347; C07C 45/52; B01J 23/18
USPC ................... 558/315; 562/532, 599; 568/486
See application file for complete search history.

(56) References Cited

U.S. PATENT DOCUMENTS

| | | | |
|---|---|---|---|
| 5,387,720 A | 2/1995 | Neher et al. | |
| 7,884,239 B2 * | 2/2011 | Fujimori | B01J 23/44 562/532 |
| 2005/0221457 A1 | 10/2005 | Tsobanakis et al. | |
| 2007/0129397 A1 | 9/2007 | Holladay et al. | |
| 2009/0298144 A1 | 12/2009 | Tsobanakis et al. | |
| 2011/0160491 A1 * | 6/2011 | Dubois | B01J 27/188 568/486 |

FOREIGN PATENT DOCUMENTS

| | | |
|---|---|---|
| JP | 2007 301506 A2 | 5/2006 |
| JP | 2010 253374 A2 | 1/2010 |
| WO | WO 2006/087084 A2 | 8/2006 |
| WO | WO 2007/058221 A1 | 5/2007 |
| WO | WO 2009/044081 A1 | 4/2009 |
| WO | WO 2009/128555 A2 | 10/2009 |
| WO | WO 2010/046227 A1 | 4/2010 |
| WO | WO 2011033689 A1 * | 3/2011 |

OTHER PUBLICATIONS

Miltenberger, K., "Hydroxycarboxylic Acids, Aliphatic" Ullmann's Encyclopedia of Industrial Chemistry (2000).*

* cited by examiner

*Primary Examiner* — Matthew P Coughlin
*Assistant Examiner* — Sagar Patel
(74) *Attorney, Agent, or Firm* — Lynn B. Morreale

(57) ABSTRACT

The present invention relates to the production of acrolein, acrylic acid or methacrylic acid by dehydration reaction of renewable raw material such as glycerin or hydroxycarboxylic acids, in the presence of a novel catalyst system supported on a carrier having a bimodal structure and a high pore volume and distribution. The dehydration reactions can be carried out for longer operation duration, so that acrolein, acrylic acid or methacrylic acid can be produced at higher productivity and for longer running time.

11 Claims, No Drawings

PROCESS OF DEHYDRATION REACTIONS

CROSS-REFERENCE TO RELATED APPLICATIONS

This application is a national stage application under 35 U.S.C. § 371 of PCT/IB2012/001574, filed Jul. 27, 2012, which claims benefit to application PCT/IB2011/002068, filed on Jul. 29, 2011.

FIELD OF THE INVENTION

The present invention relates to the production of acrolein and/or acrylic acid from glycerin and specifically to a process for preparing acrolein and acrylic acid by catalytic dehydration of glycerin in the presence of a novel catalyst system supported on a carrier having a bimodal pore structure and a high pore volume and distribution. The invention also relates to some improvements that can be brought to catalytic dehydration of hydroxycarboxylic acids or their derivatives especially 2-hydroxypropionic acid (lactic acid) or 3-hydroxypropionic acid and 2-hydroxyisobutyric acid or 3-hydroxyisobutyric acid to produce respectively renewable acrylic acid and methacrylic acid with improvement of catalysis life.

DESCRIPTION OF RELATED ART

Acrolein is used in production of methionine and is a derivative for producing amino acid used as an animal feed supplement, which has emerged as a supplement for protein. Acrolein is a synthetic intermediate of acrylic acid and leads, via reaction with methyl vinyl ether then hydrolysis, to glutaraldehyde, which has many uses in leather tanning.

Acrylic acid is a material used in a variety of industrial products and is an important monomer and comonomer of industrial polymers such as polyacrylates and polyacrylamide produced by polymerization of acrylic acid and its derivatives. One of the important applications of acrylic acid is high water-absorption resins prepared by partial neutralization of a mixture of acrylic acid and sodium acrylate or other cation. In practice, acrylic acid is polymerized and the resulting polyacrylic acid is partly neutralized. These polymers or copolymer are utilized widely in various fields such as sanitation, detergent, coating material, varnish, adhesive, paper, fabric and leather.

Methacrylic acid and its derivative methyl methacrylate are the starting materials for numerous polymerization or copolymerization reactions.

Methyl methacrylate is the monomer for the manufacture of poly(methyl methacrylate) (PMMA), known under the trademarks ALTUGLAS® and PLEXIGLAS®, being used in a variety of applications such as the car industry, household articles and office articles, the transport, building, lighting sectors.

Methyl methacrylate is also the starting material for the organic synthesis of higher methacrylates which, like it, are used in the preparation of acrylic emulsions and acrylic resins, serve as additives for poly(vinyl chloride), are used as comonomers in the manufacture of numerous copolymers such as methyl methacrylate-butadiene-styrene copolymers, serve as additives for lubricants, and have many other applications among which there may be mentioned medical prostheses, flocculants, cleaning products and the like. Acrylic emulsions and resins find applications in the paint, adhesive, paper, textile and ink sectors and the like. Acrylic resins also serve in the manufacture of plates which have the same applications as PMMA.

Acrolein and acrylic acid are produced in industrial scale by a process for oxidizing propylene by using a catalyst in the presence of oxygen. Generally, this reaction is carried in gas phase. Acrylic acid is usually produced by two step reactions. In the first step, acrolein-rich product is prepared from propylene but little acrylic acid is produced in this stage. Acrylic acid is obtained by selective oxidation of acrolein in the second step. There is no necessity to effect purification of acrolein obtained in the first step.

Starting material used in production of acrolein and acrylic acid is derived from petroleum and natural gas which are not renewable but fossil resources. However, it is very important to produce them from renewable sources to reduce the global warming effect linked to $CO_2$ emissions. Such change is the responsibility of industry major powers and can contribute to relaxation of the environmental loads and reduction of global warming gases.

Identically, the raw materials used for the synthesis of methacrylic acid or methyl methacrylate are mainly of petroleum origin or of synthetic origin. These methods thus comprise numerous sources of $CO_2$ emissions and consequently contribute to the increase in the greenhouse effect. Given the decrease in world petroleum reserves, the sources of these raw materials will gradually run out.

Glycerin, derived from animal or vegetable oils in the production of bio diesel fuels or oleochemicals is one of the raw materials envisaged as a substitute for propylene, glycerin being able to produce acrolein when subjected to a catalytic dehydration reaction. Such a process makes it possible to thus respond to the concept of green chemistry within a more general context of environment protection. Glycerin can also be produced by several processes such as fermentation and hydrogenolysis of sugar.

The process route for preparing acrylic acid from glycerin is very similar to the propylene oxidation process, since acrolein is prepared in the first step and then acrylic acid is obtained by selective oxidation of acrolein in the second step. However, in the process of dehydration reaction, a solid catalyst which is different from those used in the propylene oxidation is used, and much water together with acrolein-rich gas is supplied to the second step for producing acrylic acid. Still more, a composition of by-products is very different due to completely different reaction mechanism.

Acrylic acid may also be synthesized by dehydrating hydroxycarboxylic acids such as 2-hydroxypropionic acid (lactic acid) or 3-hydroxypropionic acid. Such processes exhibit the advantage of making possible the direct synthesis of acrylic acid from renewable raw materials.

Mention may be made also that methacrylic acid may be synthesized by dehydrating renewable hydroxycarboxylic acids such as 3-hydroxyisobutyric acid or 2-hydroxyisobutyric acid obtained for example by fermentation of biomass.

It therefore appears to be necessary to have available methods for producing at an industrial scale acrylic acid or methacrylic acid which are not dependent on a raw material of fossil origin, but which instead use biomass as raw material.

The Applicant Company has therefore sought to improve the production of acrylic acid or methacrylic acid from renewable resources using more selective catalysts that make it possible to obtain high yields of acrylic acid or methacrylic acid and that have an activity over long periods.

Numerous catalyst systems have already been the subject of studies for the dehydration reaction of glycerin to acrolein.

U.S. Pat. No. 5,387,720 describes a process for producing acrolein by dehydration of glycerol, in liquid phase or in gas phase, at a temperature ranging up to 340° C., over solid acid catalysts that are defined by their Hammett acidity. The catalysts must have a Hammett acidity below +2 and preferably below −3. These catalysts correspond, for example, to natural or synthetic siliceous materials such as mordenite, montmorillonite or acidic zeolites; supports, such as oxides or siliceous materials, for example alumina ($Al_2O_3$) or titanium oxide ($TiO_2$) covered by monobasic, dibasic or tribasic inorganic acids; oxides or mixed oxides such as gamma-alumina, $ZnO/Al_2O_3$ mixed oxide, or else heteropolyacids According to Application WO 2006/087084, the strongly acidic solid catalysts for which the Hammett acidity HO is between −9 and −18, have a strong catalytic activity for the dehydration reaction of glycerol to acrolein and are deactivated less quickly.

WO 2009/044081 discloses a glycerin dehydration reaction effected in the presence of a catalyst containing oxygen, iron, phosphorus and alkali metal and more than one alkali-earth metals selected from a group comprising Al, Si, B, Co, Cr, Ni, V, Zn, Zr, Sn, Sb, Ag, Cu, Nb, Mo, Y, Mn, Pt, Rh and rare earth.

WO2009/128555 discloses a glycerin dehydration reaction effected in the presence of a catalyst consisting of a compound in which protons in heteropolyacid are exchanged with more than one cation of elements selected from a group comprising elements belonging to Group 1 to Group 16 of periodic table.

WO2010/046227 discloses a glycerin dehydration reaction effected in the presence of a catalyst containing oxygen, phosphorus and at least one element selected from a group comprising vanadium, boron and aluminum.

WO2007/058221 discloses a process for producing acrolein by dehydration reaction of glycerin in gas-phase in the presence of heteropolyacid used as a solid acid catalyst. The heteropolyacid is those of Group 6 element such as tungstosilicic acid, tungstophosphoric acid and phosphomolybdic acid. These heteropolyacids are supported on bi-modal pore silica carrier and produce acrolein at a yield of 86%. This dehydration reaction of glycerin, however, is effected without oxidation gas but using nitrogen stream as carrier gas, so that deposition of carbon increase seriously and hence there is a problem of deterioration in time of stability, activity and selectivity of the catalysis. In preferred examples of this patent, the carrier supporting heteropolyacid has such physical properties: a specific surface of 30 to 1500 $m^2/g$, bimodal pore size distribution, a macro pore of 0.5 to 200 μm, mesopore of 1 to 50 nm, as well as a pore volume of 0.3 to 4 $cm^3/g$.

In the document JP-2010-253374, the catalyst for dehydrating glycerin without decrease of the yield of acrolein in time is obtained by essentially using a crystallized salt containing phosphorus and at least one element selected from aluminum, zirconium and boron and/or at least one element selected from rare earth elements on an amorphous porous carrier which contains ≥90 mass % silica and has micropores having 0.1-30 μm pore size and nanopores having 1-50 nm pore size.

JP-A1-2007-301506 reports that the conversion of glycerin and the yield of acrolein in catalytic glycerin dehydration can be improved by using a molded catalyst of crystalline metallosilicate having a ratio of Si/T (T=Al, B, Ti, Cu, In, Cr, Fe, Co, Ni, Zn, Ga) of less than 800, a volume-based mode diameter of the molded catalyst measured by the mercury intrusion method being smaller than 0.8 μm.

However, the catalysts recommended in the prior art for producing acrolein from glycerin generally lead to the formation of by-products such as hydroxypropanone, propanaldehyde, acetaldehyde, acetone, addition products of acrolein to glycerol, polycondensation products of glycerol, cyclic glycerol ethers, but also phenol and polyaromatic compounds which originate from the formation of coke on the catalyst and therefore from its deactivation. The presence of the by-products in acrolein, especially propanaldehyde, poses numerous problems for the separation of acrolein and requires separation and purification steps which lead to high costs for the recovery of the purified acrolein. Furthermore, when acrolein is used for producing acrylic acid, the propanaldehyde present may be oxidized to propionic acid that is difficult to separate from acrylic acid, especially by distillation. These impurities that are present greatly reduce the field of application of the acrolein produced by dehydration of glycerin for the production of acrylic acid.

Although lactic acid (2-hydroxypropionic acid) is a natural product and readily available, it is difficult to dehydrate it to acrylic acid in good yield because of competing decarbonylation and decarboxylation reactions which occur simultaneously with dehydration. The dehydration of 3-hydroxypropionic acid is accomplished relatively easily, but this hydroxycarboxylic acid is not available, and research is being conducted to produce a salt of 2-hydroxypropionic acid by fermentation, such as the ammonium salt, and to convert it to acrylic acid.

In view of the foregoing existing technologies, a process for efficiently converting hydroxycarboxylic acids and their derivatives, such as esters or salts, to unsaturated carboxylic acids, such as acrylic acid or methacrylic acid, by dehydration reaction, is still needed.

Surprisingly, in case of known dehydration catalysis in which a carrier is a porous support like bimodal porous structure, it has been observed that the meso-pore distribution decreases after the dehydration reaction whereas the macro-pore distribution doesn't change. Accordingly, the main reaction site for coking is thought to be in the mesopores, and impact of pore volume and distribution has been studied on the yield of dehydration reaction and the catalysis life.

An object of this invention is to provide a process for producing unsaturated aldehyde such as acrolein, and unsaturated carboxylic acid, especially acrylic acid and methacrylic acid, by using materials which do not derive from petroleum, at higher yield and with preventing decrease of the yield in time.

The Applicant Company has now found that particular catalytic systems supported on a bi-modal pore carrier containing a ratio in pore volume of macropores having a pore size of larger than 50 nm to the pore volume of mesopores having a pore size of 2 to 50 nm being higher than 0.5, have a high-performance catalytic activity for the dehydration of glycerin to produce acrolein while overcoming the drawbacks of the existing catalysts for this reaction.

It has furthermore become apparent to the Applicant Company that this invention could also be applied to dehydration reactions other than dehydration reaction of glycerin, and in particular to dehydration reactions of hydroxycarboxylic acids, especially 2-hydroxypropionic acid (lactic acid) or 3-hydroxypropionic acid and 2-hydroxyisobutyric acid or 3-hydroxyisobutyric acid to produce respectively renewable acrylic acid and methacrylic acid.

SUMMARY OF THE INVENTION

One subject of the present invention is therefore a process for preparing acrolein by catalytic dehydration reaction of glycerin characterized in that the dehydration reaction of glycerin is carried out in the presence of a supported catalyst comprising a W-containing metal oxide supported on a porous carrier, said porous carrier containing at least one metal oxide selected from a group comprising $TiO_2$, $SiO_2$, $Al_2O_3$, $ZrO_2$ and $Nb_2O_5$, a ratio of the pore volume of macropores having a pore size of not smaller than 50 nm to the pore volume of mesopores having a pore size of from larger than 2 nm to smaller than 50 nm being higher than 0.5, the pore volume of said porous carrier being higher than or equal to 0.30 cm$^3$/g, the pore volume being measured by the mercury intrusion method.

The present invention provides further a process for preparing acrylic acid comprising a first step of catalytic dehydration of glycerin according to the invention and a second step of gas phase oxidation of the gaseous reaction product containing acrolein formed by the dehydration reaction.

The invention further relates to a process for preparing acrylic acid and methacrylic acid by catalytic dehydration reaction of hydroxycarboxylic acid, especially 2-hydroxypropionic acid or 3-hydroxypropionic acid and 2-hydroxyisobutyric acid or 3-hydroxyisobutyric acid respectively, characterized in that the dehydration reaction of hydroxycarboxylic acid is carried out in the presence of a supported catalyst comprising a W-containing metal oxide supported on a porous carrier, said porous carrier containing at least one metal oxide selected from a group comprising $TiO_2$, $SiO_2$, $Al_2O_3$, $ZrO_2$ and $Nb_2O_5$, a ratio of the pore volume of macropores having a pore size of not smaller than 50 nm to the pore volume of mesopores having a pore size of from larger than 2 nm to smaller than 50 nm being higher than 0.5, the pore volume being measured by the mercury intrusion method.

Preferred embodiments comprise one or more of the following features:
(1) The supported catalyst comprises other metal oxide of at least one metal selected from a group comprising P, Si, Mo and V, in addition to said W-containing metal oxide.
(2) The cumulative pore volume of the bipore carrier measured by mercury intrusion method is higher than 0.30 cm$^3$/g.
(3) A mean pore diameter of the bipore carrier measured by the mercury intrusion method is larger than 30 nm.
(4) The volume-based mode diameter of the bipore carrier measured by the mercury intrusion method is larger than 50 nm.
(5) The carrier is made of $TiO_2$.
(6) The carrier is made of a compound which is a mixture of $TiO_2$ and at least one metal oxide selected from $SiO_2$, $Al_2O_3$, $ZrO_2$, and $Nb_2O_5$
(7) A salt of at least one element selected from elements belonging to the Groups 1 to 16 in the periodic table is added to the compound other than the carrier of the catalyst.
(8) The compound other than the carrier is represented by following formula (I):

$$A_a\ X_b\ W_c\ Z_d\ O_e \qquad (I)$$

in which
A is a cation selected from elements of the Groups 1 to 16 of the periodic table,
X is P, Si, Mo or V
W is tungsten
Z is more than one element selected from Ti, Cr, Mn, Fe, Co, Ni, Zn, Ga, Sn, Bi, Sb, Ce, Mg, Cs and K, a, b, c and d satisfying following rang:
$0 \leq a < 9$,
$0 \leq b \leq 1$,
$0 < c \leq 20$
$0 \leq d \leq 20$, and
e is a value determined by oxidation numbers of each element.
(9) An amount of compound represented by formula (I) is 1 to 90% by weight and preferably 3 to 60% by weight to the total weight of W-containing metal oxide and carrier.

The above processes may have following features (1) to (7) taken separately or in combination:
(1) The dehydration of glycerin is effected in the presence of oxygen gas with the conditions disclosed for example in WO 06/087083 or WO 06/114506.
(2) The dehydration of glycerin is effected in the presence of a gas containing propylene, as disclosed for example in WO 07/090,990 and WO 07/090,991, that is say to carry out the glycerin dehydration stage beneath the propylene oxidation reactor of the conventional process, taking benefit of the high temperature of the gas coming out of that stage containing mainly acrolein and some remaining propylene.
(3) The dehydration of glycerin is carried out in a plate heat exchanger type reactor or in a fixed bed reactor or in a fluidized bed type reactor or in a circulating fluidized bed or in a moving bed.
(4) The process for preparing acrylic acid from glycerin comprises a first step of catalytic dehydration of glycerin according to the invention and a second step of gas phase oxidation of the gaseous reaction product containing acrolein formed by the dehydration reaction
(5) The process for preparing acrylic acid has an intermediate step of partial condensation and removal of water and heavy by-products issuing from the dehydration step, as described for example in WO 08/087,315.
(6) The step of gas phase oxidation of the gaseous reaction product containing acrolein formed by the dehydration reaction is carried according to the methods well known to the skilled in the arts.
(7) The process for preparing acrylic acid further comprises the steps of collecting the resultant acrylic acid as a solution by using water or a solvent and then of purifying the resultant solution containing acrylic acid by using for example distillation and/or crystallization.
(8) The gaseous reaction product containing acrolein formed by the dehydration reaction is subjected to ammoxidation, as described for example in WO 08/113,927 to produce acrylonitrile
(9) Hydroxycarboxylic acids may be used in the form of their corresponding esters, such as methyl or ethyl esters, or in the form of their salts, such as ammonium salt.
(10) The process for producing acrolein or acrylic acid or methacrylic acid further comprises a step of regeneration of the dehydration catalyst with an oxygen containing gas, which is separated in time or in space Further features and advantages of the invention will appear from the following description of embodiments of the invention.

DETAILED DESCRIPTION OF THE INVENTION

The Catalyst

Physical properties of pores such as a pore diameter and a pore volume of the porous carrier according to this invention are determined by the mercury intrusion method at a mercury surface tension of 480 dyne/cm with a mercury contact angle of 140° by using Mercury Porosimetry (Pore Master 60-GT, Quanta Chrome Co.). Values or positions (nm) of mesopores and macropores shown in this specification are values of the maximum pore diameter of each pore obtained in a correlation graph having axis of ordinates of $-dV/d(\log d)$ [cm$^3$/g] which expresses how much mercury penetrate in the mercury intrusion method (expressed in cm$^3$ for logarithm μm for 1 g of sample) and axis of abscissas of the pore diameter. The standard test method is ASTM D 4284-83.

The catalyst is a supported catalyst on a bipore carrier or a carrier having bimodal porous structure.

Namely, in the bipore carrier defined in this invention, the definition of pore size of from larger than 2 nm to smaller than 50 nm for mesopore and of not smaller than 50 nm for macropore means the value of pore diameter that the peak maximal value of each pore is located at. The mesopore is in a range of from larger than 2 nm to smaller than 50 nm and preferably in a range of 10 to 30 nm. The macropore is not smaller than 50 nm and preferably in a range of 50 to 300 nm.

In the present invention, the ratio of the pore volume of macropores which are not smaller than 50 nm to the pore volume of mesopores which are within a range of from larger than 2 nm to smaller than 50 nm is higher than 0.5. This ratio is obtained by dividing a macropore volume (volume of pores having a size not smaller than 50 nm) and a mesopore volume (volume of pores having a size between from larger than 2 nm to smaller than 50 nm). In the present invention, the ratio of the macropore volume to the mesopore is higher than 0.5, preferably higher than 1.0. By selecting the above ratio, it is possible to obtain a long life catalyst for dehydration of glycerin, so that decrease in time of the conversion of glycerin and of the yield of acrolein can be prevented, in addition that acrolein can be produced at higher yield.

A feature of the pore volume (the cumulative pore volume or the total pore volume) of higher than or equal to 0.30 cm$^3$/g determined by the mercury intrusion method according to the present invention is also important. By using the porous carrier having the above pore volume preferably of higher than 0.30 cm$^3$/g, it is possible to obtain a long life catalyst for dehydration of glycerin which permits to prevent decrease in time of the conversion of glycerin and of the yield of acrolein.

Another feature of a mean pore diameter measured by the mercury intrusion method being larger than 30 nm according to in this invention is also important. The mean pore diameter is the median pore diameter or the pore diameter with assuming that the pore is cylindrical. When the cumulative pore volume is identical, if the mean pore diameter is not larger or is smaller than 30 nm, the pore volume of macropores decreases and the pore volume of mesopores increases. It was thought that the conversion of glycerin may advantageously increase when the specific surface area increase owing to increase of the pore volume of mesopores. In practice, however, decrease in catalytic activity advance rapidly because of acceleration of coking which may be caused by decrease in the efficiency of material transportation of products generated in the mesopores because of decrease of the pore volume of mesopores.

Therefore, the pore volume of the mesopores also is one of important factors which extend the catalyst life in the process according to the present invention, from such view point to increase the efficiency of the material transportation and also to prevent decrease of catalytic life caused by coking in the mesopores which is thought main reaction site.

However, to avoid a risk of decrease in mechanical strength caused by increase of mean pore diameter, in particular of pore diameter of the macropores, it is advantageous to select the mean pore size of 30 nm to 100 nm.

In this invention it is also important that the volume-based mode diameter of the bipore carrier measured by the mercury intrusion method is larger than 50 nm. Term "volume-based mode diameter" means the maximum pore diameter into which mercury penetrate mostly in volume. In the present invention, the pore diameter having the maximal value of volume in the porous carrier is larger than 50 nm. For example, in case of bipore carrier having both of mesopore and macropore, when the pore volume of macropores is higher than that of mesopores, the maximum peak of macropores is located at a pore diameter of larger than 50 nm, and when the pore volume of mesopores is higher than that of macropores, the maximum peak of mesopores is located at a pore diameter of smaller than 50 nm. For a porous carrier according to this invention, the former is preferable. In fact, it is preferable that the ratio in pore volume of the macropores to the mesopores is higher than 1.0 and that the volume-based mode diameter is higher than 50 nm.

According to another preferred embodiment of this invention, the specific surface of the porous carrier measured by BET method of nitrogen adsorption is 10 to 1000 m$^2$/g, preferably 20 to 500 m$^2$/g and more preferably 30 to 200 m$^2$/g. Increase of the specific surface may enhance higher dispersion of supported catalyst to improve activation. However, in case of the dehydration reaction of glycerin, since the reactivity of glycerin is very high and carrier itself often possesses activity, so that the carrier itself proceed successive reactions and parallel reactions. To prevent such reactions, it is necessary to increase the amount of active species on the catalyst. Therefore, preferable specific surface is 30 to 100 m$^2$/g.

The carrier and the catalyst can have any shape without limitation such as granules, powder, pellets, rings, trilobes, quadrilobes. In case of for gas phase reaction, the catalyst can be molded into sphere, cylinder, hollow cylinder, trilobe (with or without hole), quadrilobe (with or without hole) or bars, by using a molding aid if necessary. It is also possible to shape the catalyst together with carrier and optional molding aid. By using shape such as trilobes or quadrilobes, it is possible to obtain grains of catalyst with higher size leading to reduction of pressure drop while effecting reaction. Example of a particle size of molded catalyst for sphere shape is 1 to 10 mm for a fixed bed catalyst, and a particle size of not larger than 1 mm for a fluidized bed catalyst.

Preparation of the Catalyst

Source of tungsten in the W-containing metal oxide as a component to be supported on the bipore carrier is not limited specially and may be any material such as paratungstic acid or its ammonium salt, metatungstic acid or its ammonium salt, tungstic acid or its ammonium salt, tungsten oxide, tungsten chloride or organotungsten compound such as tungsten ethoxide and hexacarbonyl tungsten.

The catalyst may contain as an optional component to be supported on the bipore carrier, in addition to the above W-containing metal oxide, other metal oxide of at least one metal selected from a group comprising P, Si, Mo and V. In this case, a source material of the metal oxide is preferably heteropolyacid comprising the above elements.

Here, the heteropolyacid is explained briefly. Ions of tungsten and molybdenum become oxoacids in water and the resulting oxoacid is polymerized to form high molecular polyoxoacid. In this case, not only same kind of oxoacids are polymerized but also surrounding other oxoacid or oxoacids also are polymerized, resulting in formation of a polyacid consisting of more than two oxoacids, which is called "heteropolyacid" having a polynuclear structure. An atom that forms a center oxoacid is called as "hetero-atom", while atoms forming oxoacids surrounding the center oxoacid and forming oxoacid is called as "poly-atoms". The hetero-atom may be silicon, phosphorus, arsenic, sulfur, iron, cobalt, boron, aluminum, germanium, titanium, zirconium, cerium and chromium. Among them, phosphorus and silicon are preferable. The poly-atoms may be molybdenum, tungsten, vanadium, niobium and tantalum. In this invention, at least tungsten is always contained. Therefore, preferred heteropolyacid used in the glycerin dehydration is tungstophosphoric acid and tungstosilicic acid. The heteropolyacid may be a mixed coordinate type comprising phosphorus or silicon as the hetero-atom and molybdenum and tungsten as the poly-atoms and a mixed coordinate type of molybdenum and tungsten. It is known that the heteropolyacid have different structures such as Keggin type, Dawson type and Anderson type. The heteropolyacid possess generally such high molecular weight as 700 to 8,500. There is a dimmer thereof, which is included in this invention.

The catalyst may contain as an optional component to be supported on the bipore carrier, in addition to the above W-containing metal oxide and optionally other metal oxide of at least one element selected from a group comprising P, Si, Mo and V, at least one cation selected from the a group comprising cations belonging to Group 1 to Group 16 of the Periodic Table of Elements.

The cations belonging to Group 1 to Group 16 of the Periodic Table of Elements may be its acid salt and acid onium salts. The acid salt may be salts of sodium, potassium, rubidium, cesium, magnesium, calcium, strontium, barium, scandium, yttrium, lanthanide, titanium, zirconium, hafnium, chromium, manganese, rhenium, iron, ruthenium, osmium, cobalt, nickel, palladium, platinum, copper, silver, gold, zinc, gallium, thallium, germanium, tin, lead, bismuth and tellurium. The acid onium salts may be amine salt, ammonium salt, phosphonium salt and sulfonium salt. Sources of the acid salt and the acid onium salts may be nitrate, carbonate, sulfate, acetate, oxides and halide of the metals or oniums. Above-mentioned are simple examples but are not limit the scope of invention. An amount of metals or onium salt is 0.01 to 60% by weight, preferably 0.01 to 30% by weight with respect to W and optional at least one element selected from P, Si, Mo and V in addition to W.

The catalyst can be prepared by any known technique such as impregnation method. As materials, nitrate, ammonium salt, hydroxide, oxide, acid of each metal element which constitutes the active components of the catalyst can be used without limitation. The catalyst supporting W-containing metal oxide also can be prepared by any known technique. In practice, an aqueous solution containing compounds which contain W and optional element selected from P, Si, Mo and V in addition to W is prepared firstly. In case of heteropolyacid also, an aqueous solution thereof is firstly prepared. Or, their aqueous solutions can be prepared after water contained in the heteropolyacid in a form of adsorptive water and crystal water is removed partially or totally under vacuum or heat-drying.

The resulting aqueous solution of W-containing metal oxide is added with a carrier containing at least one metal oxide selected from a group comprising $TiO_2$, $SiO_2$, $Al_2O_3$, $ZrO_2$ and $Nb_2O_5$. Optionally, an aqueous solution containing a compound or compounds containing halide, carbonate, acetate, nitrate, oxalate, phosphate, sulfate, hydroxide of metal or onium of element belonging to Group 1 to Group 16 of the Periodic Table of Elements is added. The resulting mixture is subjected to filtration or drying under reduced pressure to obtain a solid which is then calcinated finally.

Addition of the salts of metal or onium of element belonging to Group 1 to Group 16 of the Periodic Table of Elements can be effected after, before or during addition of the aqueous solution containing compounds which contain W and optional element selected from P, Si, Mo and V in addition to W to porous carrier.

The calcination and drying can be carried out successively for each addition of catalytic component to carrier, or can be done after all catalytic components are added.

In one embodiment, the preparation of the catalyst comprises more than one cycle of contacting a carrier with a solution of the active components of the catalyst, drying and calcining the resulting solid mixture. The contacting may be performed by techniques of pore volume impregnation or excess solution impregnation. The multiple contacting procedure may be performed with different solutions at each step.

The calcination can be carried out in air or under inert gas such as nitrogen, helium and argon or under an atmosphere of a mixed gas of air and inert gas. The calcination is effected advantageously under an atmosphere of air which facilitates operations. Furnace for calcination is not limited specially and can be muffle furnace, rotary kiln, fluidized bed furnace. The calcination can be effected even in a reaction tube which is used for the glycerin dehydration reaction.

Selection of the firing temperature of 400 to 900° C. is another important feature of this invention. In fact, in dehydration reactions, formation or precipitation of cokes per unit time is extremely large, so that the life of catalyst is short, resulting in that much frequent regeneration of catalyst is required. The regeneration can be carried out by a circulation of oxygen-containing gas which generates a large quantity of heat to remove cokes by burning. Sufficient burning and removal of cokes can't be expected at lower temperatures. In any way, the catalyst is exposed after all to a high temperature during reaction and regeneration stage even if the calcination of catalyst is effected at lowered temperature. Therefore, in case of a catalyst which had been fired at lower temperature, there may be a difference in performance between at an initial of reaction and after regeneration.

In order to realize the same or constant performance after several reaction and regeneration cycles as at the initial reaction, and hence to facilitate operations in reaction and regeneration, it is advantageous to effect calcination at higher temperature. In case of heteropolyacid such as phosphotungstic acid and tungstosilicic acid, decomposition of their structures starts at about 350° C. and the structure of heteropolyacid will be lost when it is heated above this temperature. In case of phosphotungstic acid, it will change to oxides of phosphorus and tungsten or to complex oxide other than heteropolyacid. Use of heteropolyacid such as phosphotungstic acid as a raw material of W is suitable, but it does not show the structure of heteropolyacid because the firing temperature of 400 to 900° C. which is one of features of this invention. The firing temperature is preferably 450 to 800° C. and the firing time duration is preferably 0.5 to 10 hours.

Dehydration of Glycerin

The dehydration reaction of glycerin according to this invention can be carried out in gas phase or in liquid phase and the gas phase is preferable. The gas phase reaction can be carried out in a variety of reactors such as fixed bed, fluidized bed, circulating fluidized bed and moving bed. Among them, the fixed bed or the fluidized bed is preferable. Regeneration of the catalyst can be effected outside the reactor. When the catalyst is taken out of a reactor system for regeneration, the catalyst is burnt in air or in oxygen-containing gas. Regeneration of the catalyst can also be effected within the reactor, with cycles that comprise a reaction period and a regeneration period. During the regeneration period, air or an oxygen-containing gas is injected in the reactor. Preferably, two or more reactors are used in parallel so that at any time part of the reactors are used in reaction mode and part of them are used in regeneration mode.

In case of liquid phase reaction, usual general reactors for liquid reactions for solid catalysts can be used. Since the difference in boiling point between glycerin (290° C.) and acrolein and acrylic acid is big, the reaction is effected preferably at relatively lower temperatures so as to distil out acrolein continuously.

The reaction temperature for producing acrolein and acrylic acid by dehydration of glycerin in gas phase is effected preferably at a temperature of 200° C. to 450° C. If the temperature is lower than 200° C., the life of catalyst will be shortened due to polymerization and carbonization of glycerin and of reaction products because the boiling point of glycerin is high. On the contrary, if the temperature exceeds 450° C., the selectivity of acrolein and acrylic acid will be lowered due to increment in parallel reactions and successive reactions. Therefore, more preferable reaction temperature is 250° C. to 350° C. The catalyst regeneration is effected at a reactor temperature of 250° C. to 450° C. and preferably between 290° C. and 370° C.

The pressure is not limited specially but is preferably lower than 5 atm and more preferably lower than 3 atm. Under higher pressures, evaporated glycerin will be condensed and deposition of carbon will be promoted by higher pressure so that the life of catalyst will be shortened.

A feed rate of a material gas is preferably 500 to 10,000 $h^{-1}$ in term of the space velocity of GHSV (Gas Hourly Space Velocity, defined as the ratio between the gas flow rate in Normal Temperature and Pressure conditions and the volume of catalyst). The selectivity will be lowered if the GHSV becomes lower than 500 $h^{-1}$ due to successive reactions. On the contrary, if the GHSV exceeds 10,000 $h^{-1}$, the conversion will be lowered.

The reaction temperature of the liquid phase reaction is preferably from 150° C. to 350° C. The selectivity will be reduced under highest temperatures although the conversion is improved. The reaction pressure is not limited specially but the reaction can be carried if necessary under a pressurized conditions of 3 atm to 70 atm.

The material of glycerin is easily available in a form of aqueous solution of glycerin. In the invention, glycerin or glycerol may be used.

The gases fed to the reactor comprise glycerol, water, oxygen and inert gases such as nitrogen, argon, CO, $CO_2$.

The water to glycerol weight ratio which is fed to the reactor is 20/1 to 1/20 and preferably 5/1 to 1/2 and most preferably 4/1 to 1/1.

The concentration of glycerin in a mixed gas which is fed in the process of the invention is 1 to 30 mol %, preferably 1 to 12 mol % and more preferably 3 to 10 mol %. Too high concentration of glycerin will result in such problems as production of glycerin ethers or undesirable reaction between the resulting acrolein and acrylic acid and material glycerin. Temperature that is necessary to evaporate glycerin is increased.

The glycerin dehydration reaction of this invention is advantageously carried out in the presence of oxygen-containing gas such as oxygen or air. A concentration of oxygen is 1 to 10 mol %, preferably 2 to 7 mol %).

Dehydration Reactions of Hydroxycarboxylic Acids

The dehydration reactions of hydroxycarboxylic acids such as 2-hydroxypropionic acid or 3-hydroxypropionic acid and 2-hydroxyisobutyric acid or 3-hydroxyisobutyric acid can be carried out in the vapor phase or in the liquid phase in a variety of reactors such as fixed bed, fluidized bed, circulating fluidized bed and moving bed. Among them, the fixed bed or the fluidized bed are preferable.

Dehydration reaction temperature is generally from 100° C. to 400° C., preferably from 200° C. to 350° C., and the pressure is about from 0.5 to 5 atm.

Vapor phase reactions normally require higher temperatures than liquid phase reactions.

It is possible and often desirable to include an inert gas such as nitrogen or recycle gas in the feed along with the hydroxycarboxylic acid.

In the dehydration reaction of 2-hydroxypropionic acid or 3-hydroxypropionic acid to produce acrylic acid, the partial pressure is generally between 1 and 10%, preferably between 2 and 6%.

In the dehydration reaction of 2-hydroxyisobutyric acid or 3-hydroxyisobutyric acid to produce methacrylic acid, the partial pressure is generally between 1 and 20%, preferably between 2 and 10%.

The time for the conversion of the hydroxcarboxylic acid will vary. Reactions in the vapor phase are generally faster than those run in the liquid phase and occur within a few seconds, while reactions in the liquid phase can take from about 1 to about 6 hours. The contact time in the vapor phase is normally 0.1-15, usually 2-4 seconds.

The amount of dehydration catalyst according to the invention is subject to considerable variation and is not critical.

In the processes of the invention, by using the improved catalyst, the dehydration reactions can be carried out for longer operation duration, so that acrolein, acrylic acid or methacrylic acid can be produced at higher productivity and for longer running time.

Owing to improvement of catalysis life, the efficiencies of catalytic reaction and of regeneration cycle of catalyst can be improved, so that complicated operations can be simplified, which is very beneficial for industrial plants. Mainly, with longer catalyst life in a fixed bed reactor, the number of reactors needed for a continuous operation is reduced since the cycle length for each reactor is longer. This contributes in a significant capital cost reduction. Longer catalyst cycle life give also more degree of freedom to optimise the regeneration parameters, since the duration of the regeneration can be extended, either to have a more complete regeneration of the catalyst, or preferably to operate the catalyst regeneration at a lower average temperature. A lower catalyst regeneration is preferable since it limits the catalyst degradation by high process temperature. It has been discovered that the bipore catalyst can be regenerated efficiently at a temperature comprised between 250 and 350° C., within the same duration than the catalyst reaction cycle.

When the catalyst is used in a fluid bed, the regeneration can be done continuously using an internal or external regenerator. With the bipore catalyst of extended life it is possible to use a smaller regenerator.

Finally, whatever the reactor technology, a catalyst having an extended life, requires less oxygen to be co-fed during the catalyst reaction cycle. Thereby reducing the flammability issues, especially in downstream equipments like absorption units.

Manufacturing Acrylic Acid

The resulting acrolein from the catalytic dehydration of glycerin is further oxidized to produce acrylic acid, according to the methods well known to the skilled.

In one embodiment, the process for preparing acrylic acid from glycerin comprises an intermediate step of partial condensation and removal of water and heavy by-products issuing from the dehydration step.

The said intermediate step has the aim of removing most of the water present and the heavy by-products before sending the gaseous stream comprising the acrolein and all non-condensable gases to the step for the oxidation of acrolein to give acrylic acid. This partial condensation of the water thus makes it possible to avoid damage to the catalyst of the oxidation of acrolein to give acrylic acid and to avoid, during the subsequent stages, the removal of large amounts of water, which could well be expensive and result in losses of acrylic acid. In addition, it makes it possible to remove a portion of the "heavy" impurities formed during the dehydration of the glycerol and to facilitate purification operations.

This intermediate step is carried out on a separating unit which is a condensation plant comprising an absorption column coupled or not coupled to an evaporator, one or more heat exchangers, one or more condensers, a dephlegmator, and any item of equipment well known to a person skilled in the art which makes it possible to carry out a partial condensation of an aqueous stream.

It is carried out under conditions such that the acrolein-rich stream is separated into an acrolein-rich gaseous phase and an acrolein-poor aqueous phase.

From 20 to 95%, preferably from 40 to 90%, of the water present in the stream is removed in the liquid stream and the acrolein-rich phase generally comprises more than 80% and preferably more than 90% of the acrolein initially present in the stream. This result is generally obtained by lowering the temperature to a temperature of 60° C. to 120° C.

The process for preparing acrylic acid according to the invention further comprises the steps of collecting the resultant acrylic acid as a solution by using water or a solvent, and then of purifying the resultant solution containing acrylic acid by using for example a distillation step for removing low- and high-boiling point materials and/or a crystallization step for purifying acrylic acid by crystallizing it.

The acrylic acid thus obtained can be used to produce for example polyacrylic acids or salts as water-soluble polymers or water-absorbent resins, by known methods.

Now, the present invention will be explained in detail with referring illustrative examples but this invention should not be limited to those described in following examples. In the following Examples and Comparative Examples, % means mole %.

EXPERIMENTAL SECTION

Preparation of Catalysts

Example 1

Catalyst of $PW/TiO_2$ for dehydration reaction of glycerin was prepared as following: 13.2 g of phosphotungstic acid (Nippon Inorganic Color & Chemical Co., Ltd.) were dissolved in 100 ml of pure water to obtain an aqueous solution of phosphotungstic acid. Separately, 100 g of Anatase $TiO_2$ pellets (Saint-Gobain ST 31119: diameters of 3.2 mm×length of 5 mm, 48.2 $m^2/g$, 0.36 $cm^3/g$, a pore volume ratio=1.4) was placed on a porcelain dish onto which the above aqueous solution of phosphotungstic acid was added. After an assembly was left for 2 hours, the aqueous solution of phosphotungstic acid was dried-up at 120° C. for 10 hours and then calcinated in an atmosphere of air at 500° C. for 3 hours.

Example 2

Example 1 was repeated, except Anatase $TiO_2$ pellet (Saint-Gobain ST 31119: diameters of 3.2 mm×length of 5 mm, 29.2 $m^2/g$, 0.30 $cm^3/g$, the pore volume ratio=1.5) was used as $TiO_2$.

Example 3

Example 1 was repeated, except Anatase $TiO_2$ pellet (Saint-Gobain ST 31119: diameters of 3.2 mm×length of 5 mm, 35.6 $m^2/g$, 0.33 $cm^3/g$, the pore volume ratio=1.1) was used as $TiO_2$.

The cumulative pore volume, the ratio of pore volume and the mean pore diameter of Examples 2 and 3 are within a range of this invention.

Example 4

Example 1 was repeated, except Anatase $TiO_2$ pellet (Saint-Gobain ST 31119: diameters of 3.2 mm×length of 5 mm, 39.9 $m^2/g$, 0.36 $cm^3/g$, the pore volume ratio=1.3) was used as $TiO_2$.

Example 5

Example 1 was repeated, except Anatase $TiO_2$ pellet (Saint-Gobain ST 31119: diameters of 3.2 mm×length of 5 mm, 45.6 $m^2/g$, 0.36 $cm^3/g$, the pore volume ratio=1.4) was used as $TiO_2$.

Example 6

Catalyst of $W/TiO_2$ for dehydration reaction of glycerin was prepared as following: 12.2 g of ammonium metatungstate (Nippon Inorganic Color & Chemical Co., Ltd.) were dissolved in 100 ml of pure water to obtain an aqueous solution of ammonium metatungstate. Separately, 100 g of Anatase $TiO_2$ pellets (Saint-Gobain ST 31119: diameters of 3.2 mm×length of 5 mm, 48.2 $m^2/g$, 0.36 $cm^3/g$, a pore volume ratio=1.4) was placed on a porcelain dish onto which the above aqueous solution of was added. After an assembly was left for 2 hours, the aqueous solution of ammonium metatungustate was dried up at 120° C. for 10 hours and then calcinated in an atmosphere of air at 500° C. for 3 hours.

Example 7

Example 1 was repeated, except Anatase $TiO_2$ ring (Saint-Gobain ST 31119: diameters of 4.5 mm×length of 5 mm, 54 $m^2/g$, 0.32 $cm^3/g$, the pore volume ratio=0.5) was used as $TiO_2$.

Example 8

Example 1 was repeated, except Anatase TiO$_2$ trilobes (Saint-Gobain ST 31119: diameters of 4.5 mm×length of 5 mm, 53 m$^2$/g, 0.40 cm$^3$/g, the pore volume ratio=0.9) was used as TiO$_2$.

Example 9

Example 1 was repeated, except Anatase TiO$_2$ quadrilobes (Saint-Gobain ST 31119: diameters of 4.5 mm×length of 5 mm, 54 m$^2$/g, 0.38 cm$^3$/g, the pore volume ratio=0.9) was used as TiO$_2$.

Comparative Example 1

In Comparative Example 1, a sample which is outside the scope of invention was prepared and evaluated.

Example 1 was repeated, except Anatase TiO$_2$ pellet (Sakai Chemistry CS-300 S: diameter of 3.0 mm, 75 m$^2$/g, 0.40 cm$^3$/g, the pore volume ratio=0.4) was used as TiO$_2$.

Comparative Example 1 is outside the present invention because the ratio in pore volume of the macropores to the mesopores is 0.4 which is outside a requirement of higher than 0.5 of this invention. In fact, its mean pore diameter is as small as 23.2 nm due to larger pore volume of the mesopores, and is outside a requirement of larger than 30 nm of this invention.

Comparative Example 2

Example 1 was repeated, except Anatase TiO$_2$ pellet (Sakai Chemistry CS-300 S: diameter of 3.5 mm, 52 m$^2$/g, 0.32 cm$^3$/g, the pore volume ratio=0.3) was used as TiO$_2$.

Catalysts of Comparative Examples 1 and 2 have same or higher pore volume and specific surface as Examples 1, 4 and 5.

Comparative Example 3

Example 1 was repeated, except Anatase TiO$_2$ pellet (Saint-Gobain ST 31119: diameters of 3.2 mm×length of 5 mm, 42.4 m$^2$/g, 0.26 cm$^3$/g, a pore volume ratio=1.6) was used as TiO$_2$.

This catalyst of Comparative Example 3 has similar specific surface, mean pore diameter and pore volume as Examples 1 and 5 and satisfy required their ranges in physical properties, but the pore volume of 0.26 cm$^3$/g is outside the claimed range of higher than 0.30 cm$^3$/g of this invention.

Comparative Example 4

Example 6 was repeated, except Anatase TiO$_2$ pellet (Saint-Gobain ST 31119: diameters of 3.2 mm×length of 5 mm, 42.4 m$^2$/g, 0.26 cm$^3$/g, a pore volume ratio=1.6) was used as TiO$_2$.

By comparing Comparative Example 4 and Example 6, difference in physical properties of TiO$_2$ when the carrier supports a metal oxide consisting of tungsten oxide alone can be evaluated in comparison to other W-containing metal oxides. In fact, the carrier of Comparative Example 4 has same specific surface, mean pore diameter and the ratio in pore volumes as Example 6 and satisfy required their ranges in physical properties, but the pore volume of 0.26 cm$^3$/g is outside the claimed range of higher than 0.30 cm$^3$/g of this invention, as is the case of PW/TiO$_2$ in Comparative Example 3.

The characteristics of these catalysts are summarized in Table 1

TABLE 1

| Catalyst | Total pore volume (cm$^3$/g) | Ratio of pore volumes of macropore/mesopore | Mean pore diameter (nm) | Pore diameter of mesopore at peak maximum (nm) | Pore diameter of macropore at peak maximum (nm) | volume-based mode diameter (nm) | specific surfaca area (m$^2$/g) |
|---|---|---|---|---|---|---|---|
| Example 1 | 0.36 | 1.4 | 37.5 | 18.5 | 130 | 130 | 48.2 |
| Example 2 | 0.30 | 1.5 | 47.9 | 22.2 | 149 | 149 | 29.2 |
| Example 3 | 0.33 | 1.1 | 36.6 | 20.7 | 136 | 136 | 35.6 |
| Example 4 | 0.36 | 1.3 | 39.7 | 19.9 | 160 | 160 | 39.9 |
| Example 5 | 0.36 | 1.4 | 37.6 | 18.4 | 159 | 159 | 45.6 |
| Example 6 | 0.36 | 1.4 | 37.5 | 18.5 | 130 | 130 | 48.2 |
| Example 7 | 0.32 | 0.5 | 22.6 | 19.9 | 83 | 20 | 54 |
| Example 8 | 0.40 | 0.9 | 44.1 | 20.5 | 134 | 134 | 53 |
| Example 9 | 0.38 | 0.9 | 34.1 | 19.9 | 127 | 127 | 54 |
| Comparative Example 1 | 0.40 | 0.4 | 23.2 | 16.6 | 452 | 16.6 | 75.0 |
| Comparative Example 2 | 0.32 | 0.3 | 23.9 | 18.9 | 140 | 18.9 | 52.0 |
| Comparative Example 3 | 0.26 | 1.6 | 33.9 | 14.8 | 155 | 155 | 42.4 |
| Comparative Example 4 | 0.26 | 1.6 | 33.9 | 14.8 | 155 | 155 | 42.4 |

Reactivity of Catalysts

The catalysts were subjected to evaluation test in a pass-through type fixed bed reactor operated at ambient pressure. 30 cm$^3$ of catalyst was packed in a SUS reaction tube (20 mm diameter). An aqueous solution of 50 wt % of glycerin was pre-heated in a vaporizer heated at 330° C. and the resulting gasified glycerin was fed directly to the catalytic bed together with air at a flow rate of 23.4 h/hr. The reactor containing the catalyst was heated at 290° C. The feed stream have following composition:glycerin:oxygen:nitrogen:water=4.7 mol %:2.8 mol %:68.5 mol %:24.0 mol %. GHSV was 2,020 h$^{-1}$.

Products were collected in a condenser as condensates and the quantitative determination of all components was carried out by a gas chromatograph (Agilent 7890A, DB-WAX column). Factor of each product was corrected by the gas chromatograph to obtain absolute contents of glycerin fed, glycerin remained and products for determining the conversion of raw material (glycerin conversion), the selectivity of targeted substance (acrolein selectivity) the yield of objective substance (acrolein yield) were calculated by following equations:

The conversion of material (%)=(a mole number of material reacted/a mole number of material fed)*100

The selectivity of objective substance (%)=(a mole number of objective substance obtained/a mole number of material reacted)*100

The yield of objective substance (%)=(a mole number of objective substance obtained/a mole number of material fed)*100

The quantitative analysis was carried out in every several hours and the glycerin conversion and the acrolein yield were compared between a reaction time of 19 hrs and a reaction time of 43 hours.

Results are shown in Table 2.

TABLE 2

| Catalyst | Reaction time 19 hr | | Reaction time 43 hr | |
|---|---|---|---|---|
| | Conversion of glycerin, % | Yield of acrolein, % | Conversion of glycerin, % | Yield of acrolein, % |
| Example 1 | 99.6 | 77.0 | 95.6 | 73.6 |
| Example 2 | 97.9 | 76.7 | 88.4 | 67.8 |
| Example 3 | 98.2 | 75.0 | 89.4 | 67.0 |
| Example 4 | 99.5 | 77.4 | 93.2 | 70.9 |
| Example 5 | 99.7 | 76.9 | 94.8 | 72.1 |
| Example 6 | 99.6 | 74.3 | 93.6 | 68.3 |
| Example 7 | 99.6 | 74.2 | 93.6 | 71.6 |
| Example 8 | 99.4 | 74.5 | 94.7 | 69.4 |
| Example 9 | 98.8 | 72.8 | 91.4 | 65.2 |
| Comparative Example 1 | 99.3 | 73.5 | 88.2 | 64.8 |
| Comparative Example 2 | 96.8 | 70.4 | 78.0 | 56.2 |
| Comparative Example 3 | 96.3 | 76.0 | 83.1 | 64.8 |
| Comparative Example 4 | 95.4 | 73.4 | 78.9 | 58.9 |

Catalyst of example 7 was also tested in the following conditions.

The feed stream I was composed of: glycerin:oxygen:nitrogen:water=6.0 mol %:2.0 mol %:61.3 mol %:30.7 mol %. GHSV was 2,020 $h^{-1}$. Acrolein yield after 19 hr on stream is 73.5%.

The cumulative pore volume, the ratio of pore volume and the mean pore diameter of Examples 2 and 3 are within a range of this invention. Results reveal that these catalysts show high glycerin conversion and high acrolein yield and reduced decrease of the glycerin conversion and of the acrolein yield, in spite of relatively lower specific surface area to Comparative Examples.

Catalysts of Comparative Examples 1 and 2 have same or higher pore volume and specific surface as Examples 1, 4 and 5, but the catalytic activity decrease much rapidly (comparison in the glycerin conversion and the acrolein yield between 19 hr and 43 hr). Results reveal that the life of catalyst is influenced by the ratio of pore volumes and the mean pore diameter.

With regards to comparative example 3, the result reveals that deterioration in time of the glycerin conversion and of the acrolein yield is influenced also by the cumulative pore volume in addition to the ratio of specific surface, mean pore diameter and the ratio of pore volumes.

By comparing Comparative Example 4 and Example 6, the result reveals that deterioration in time of the glycerin conversion and of the acrolein yield is influenced also by the ranges of physical properties when a porous carrier supports a metal oxide consisting of tungsten oxide alone.

With regards to Examples 7-9, the result reveals that the shape of the carrier/catalyst such as rings, trilobes or quadrilobes leads to high conversion and yield maintained for a long time.

From these results of Examples and Comparative Examples, following conclusions are obtained:

(1) When a catalyst comprising a W-containing metal oxide and optionally other metal oxide containing at least one element selected from P, Si, Mo and V supported on a bipore carrier containing at least one metal oxide selected from a group comprising $TiO_2$, $SiO_2$, $Al_2O_3$, $ZrO_2$ and $Nb_2O_5$, a ratio of the pore volume of macropores having a pore size of not smaller than 50 nm to the pore volume of mesopores having a pore size of from larger than 2 nm to smaller than 50 nm being higher than 0.5, there is no substantial difference in glycerin conversion and in acrolein yield after the reaction time of 19 hours and 43 hours, so that the life of catalyst is improved.

(2) In case of known catalysis in which a carrier is a porous support like bipore and has a higher pore volume than 0.3 $cm^3/g$, no decrease in time of glycerin conversion and of acrolein yield is realized so that long life of catalyst can be expected. Still more, there is such risk that mechanical strength is lost simply when the pore volume is increased. Advantage of the higher pore volume and hence longer catalyst life can be obtained only when all requirement of the ratio in pore volume of macropores to the mesopores, and hence the mean pore diameter and the volume-based mode diameter according to the present invention are satisfied, resulting in that the life of catalyst is improved.

(3) In other words, decrease in time of catalytic activity or the life of catalyst can be improved without spoiling the glycerin conversion and the acrolein yields, comparing to $TiO_2$ having physical properties outside the present invention, when a catalyst comprising a W-containing metal oxide and optionally other metal oxide containing at least one element selected from P, Si, Mo and V supported on a bipore carrier containing at least one metal oxide selected from a group comprising $TiO_2$, $SiO_2$, $Al_2O_3$, $ZrO_2$ and $Nb_2O_5$, in particular bipore $TiO_2$ carrier having a bimodal pore structure, a ratio of the pore volume of macropores having a pore size of not smaller than 50 nm to the pore volume of mesopores having a pore size of from larger than 2 nm to smaller than 50 nm being higher than 0.5, in particular higher than 1.0, a mean pore diameter of larger than 30 nm and the volume-based mode diameter of larger than 50 nm, and the pore volume of said porous carrier being higher than or equal to 0.30 $cm^3/g$.

The invention claimed is:

1. A process for preparing acrolein by catalytic dehydration reaction of glycerin comprising the step of dehydrating glycerin in the presence of a supported catalyst comprising a W-containing metal oxide supported on a bipore or bimodal porous carrier, said porous carrier being made of $TiO_2$ or a compound which is a mixture of $TiO_2$ and at least one metal oxide selected from $SiO_2$, $Al_2O_3$, $ZrO_2$ or $Nb_2O_5$, wherein the W-containing metal oxide is represented by formula (I):

$$A_a X_b W_c Z_d O_e \quad (I)$$

wherein A is a cation selected from the group consisting of elements of Periodic Table Groups 1 to 16, X is selected from the group consisting of P, Si, Mo and V, W is tungsten, Z is at least one element selected from the group consisting of Ti, Cr, Mn, Fe, Co, Ni, Zn, Ga, Sn, Bi, Sb, Ce, Mg, Cs and K, a, b, c and d satisfy the following ranges: $0 \leq a < 9$; $0 \leq b \leq 1$; $0 < c \leq 20$; $0 \leq d \leq 20$; and e is a value determined by oxidation numbers of each element and which is not 0; and wherein a ratio in the pore volume of macropores having a pore size of not smaller than 50 nm to the pore volume of mesopores having a pore size of from larger than 2 nm to smaller than 50 nm being higher than 0.5, the pore volume of said porous carrier being higher than or equal to 0.30 cm$^3$/g, the pore volume being measured by the mercury intrusion method, and wherein a mean pore diameter of said porous carrier measured by the mercury intrusion method is between 30 nm to 100 nm.

2. The process according to claim 1, wherein the supported catalyst comprises another metal oxide, in addition to said W-containing metal oxide, of at least one metal selected from the group consisting of P, Si, Mo, and V.

3. The process according to claim 1, wherein the pore volume of said porous carrier measured by mercury intrusion method is higher than 0.30 cm$^3$/g.

4. The process according to claim 1, wherein the mean pore diameter of said porous carrier measured by the mercury intrusion method is larger than 50 nm.

5. The process according to claim 1, wherein a salt of at least one element selected from elements belonging to Periodic Table Groups 1 to 16 is added to the catalyst other than the carrier.

6. The process according to claim 1, wherein said metal oxide represented by the formula (I) has a weight that is from 1% to 90% of the weight of said carrier.

7. A process for preparing acrylic acid from glycerin comprising a first step of catalytic dehydration of glycerin according to claim 1 to form a gaseous reaction product containing acrolein and a second step of gas phase oxidation of the gaseous reaction product containing acrolein formed by the dehydration reaction.

8. The process according to claim 7, further comprising an intermediate step of partial condensation and removal of water and heavy by-products issuing from the dehydration step.

9. The process according to claim 8, further comprising steps of (i) collecting resultant acrylic acid as a solution-containing-acrylic acid by using water or a solvent and (ii) purifying solution-containing-acrylic acid using distillation and/or crystallization.

10. A process for preparing acrylonitrile from glycerin comprising a first step of catalytic dehydration of glycerin according to claim 1 and a second step of ammoxidation of gaseous reaction product containing acrolein formed by the dehydration.

11. A process for preparing acrylic acid and methacrylic acid by catalytic dehydration reaction of hydroxycarboxylic acid, wherein the dehydration reaction of hydroxycarboxylic acid is carried out in the presence of a supported catalyst comprising a W-containing metal oxide supported on a bipore or bimodal porous carrier, said porous carrier containing at least one metal oxide selected from the group consisting of TiO$_2$, SiO$_2$, Al$_2$O$_3$, ZrO$_2$ and Nb$_2$O$_5$, a ratio of the pore volume of macropores having a pore size of not smaller than 50 nm to the pore volume of mesopores having a pore size of from larger than 2 nm to smaller than 50 nm being higher than 0.5, the pore volume being measured by the mercury intrusion method, and wherein a mean pore diameter of said porous carrier measured by the mercury intrusion method is between 30 nm to 100 nm.

* * * * *